United States Patent
Hunt et al.

(10) Patent No.: US 11,090,495 B2
(45) Date of Patent: *Aug. 17, 2021

(54) SYSTEMS AND METHODS FOR ALERTING AUDITORY PROSTHESIS RECIPIENT

(71) Applicant: COCHLEAR LIMITED, Macquarie University (AU)

(72) Inventors: Andrew Hunt, Macquarie University (AU); David Harte, Macquarie University (AU); Hans Yoo, Macquarie University (AU); Roger Alan Smith, Macquarie University (AU)

(73) Assignee: Cochlear Limited, Macquarie University (AU)

(*) Notice: Subject to any disclaimer, the term of this patent is extended or adjusted under 35 U.S.C. 154(b) by 0 days.

This patent is subject to a terminal disclaimer.

(21) Appl. No.: 16/737,392

(22) Filed: Jan. 8, 2020

(65) Prior Publication Data
US 2020/0222705 A1 Jul. 16, 2020

Related U.S. Application Data

(63) Continuation of application No. 15/199,029, filed on Jun. 30, 2016, now Pat. No. 10,543,371.

(60) Provisional application No. 62/187,052, filed on Jun. 30, 2015.

(51) Int. Cl.
| | |
|---|---|
| *H04R 25/00* | (2006.01) |
| *A61N 1/372* | (2006.01) |
| *A61N 1/05* | (2006.01) |
| *A61N 1/36* | (2006.01) |

(52) U.S. Cl.
CPC ....... *A61N 1/37258* (2013.01); *A61N 1/0541* (2013.01); *A61N 1/36036* (2017.08); *A61N 1/36038* (2017.08)

(58) Field of Classification Search
CPC ................................................. A61N 1/37258
USPC ........................................................... 607/57
See application file for complete search history.

(56) References Cited

U.S. PATENT DOCUMENTS

| | | | | |
|---|---|---|---|---|
| 8,452,412 | B2 | 5/2013 | Ibrahim | |
| 9,119,009 | B1* | 8/2015 | Folkmanis | H04R 25/55 |
| 10,543,371 | B2 | 1/2020 | Hunt et al. | |
| 10,556,110 | B2* | 2/2020 | Meskens | A61N 1/0541 |
| 2013/0090517 | A1* | 4/2013 | Van den Heuvel | A61N 1/37264 600/25 |
| 2013/0109909 | A1* | 5/2013 | van Gerwen | H04R 25/554 600/25 |
| 2014/0275730 | A1* | 9/2014 | Lievens | H04R 25/70 600/25 |
| 2014/0379047 | A1 | 12/2014 | Meskens | |

(Continued)

*Primary Examiner* — Phylesha Dabney
(74) *Attorney, Agent, or Firm* — Edell, Shapiro & Finnan, LLC (57) ABSTRACT

An alert system detects when an auditory prosthesis recipient is wearing her sound processor. When the processor is not worn, the alert system signals a secondary device, such as an accessory, to provide some other form of tactile stimulation to allow the recipient to be made aware of certain auditory stimuli she is not receiving via the auditory prosthesis. Thus, the alert system can effectively "hear" for the recipient. Since many auditory prosthesis recipients are, for all practical purposes, completely deaf without their external sound processors attached and operational, such an alert system increases the recipient's safety, convenience, and quality of life.

20 Claims, 9 Drawing Sheets

(56) References Cited

U.S. PATENT DOCUMENTS

| | | |
|---|---|---|
| 2016/0059014 A1 | 3/2016 | Johnston et al. |
| 2016/0088405 A1* | 3/2016 | Wernaers ............. H04R 25/558 |
| | | 381/315 |
| 2016/0088406 A1* | 3/2016 | Wernaers ............. H04R 25/505 |
| | | 381/317 |
| 2017/0001008 A1* | 1/2017 | Hunt .................. A61N 1/36036 |
| 2017/0360364 A1 | 12/2017 | Heasman et al. |
| 2017/0360365 A1 | 12/2017 | Heasman et al. |

* cited by examiner

SYSTEMS AND METHODS FOR ALERTING AUDITORY PROSTHESIS RECIPIENT

CROSS-REFERENCE TO RELATED APPLICATIONS

This application is a continuation of U.S. patent application Ser. No. 15/199,029, which was filed on Jun. 30, 2016, issued as U.S. Pat. No. 10,543,371, and claims the benefit of U.S. Provisional Patent Application No. 62/187,052, which was filed Jun. 30, 2015. The disclosure of these priority applications is hereby incorporated by reference in their entirety into the present application.

BACKGROUND

Hearing loss, which can be due to many different causes, is generally of two types: conductive and sensorineural. Sensorineural hearing loss is due to the absence or destruction of the hair cells in the cochlea that transduce sound signals into nerve impulses. Various hearing prostheses are commercially available to provide individuals suffering from sensorineural hearing loss with the ability to perceive sound. For example, cochlear implants use an electrode array implanted in the cochlea of a recipient (i.e., the inner ear of the recipient) to bypass the mechanisms of the middle and outer ear. More specifically, an electrical stimulus is provided via the electrode array to the auditory nerve, thereby causing a hearing percept.

Conductive hearing loss occurs when the normal mechanical pathways that provide sound to hair cells in the cochlea are impeded, for example, by damage to the ossicular chain or the ear canal. Individuals suffering from conductive hearing loss can retain some form of residual hearing because some or all of the hair cells in the cochlea function normally.

Individuals suffering from conductive hearing loss often receive a conventional hearing aid. Such hearing aids rely on principles of air conduction to transmit acoustic signals to the cochlea. In particular, a hearing aid typically uses an arrangement positioned in the recipient's ear canal or on the outer ear to amplify a sound received by the outer ear of the recipient. This amplified sound reaches the cochlea causing motion of the perilymph and stimulation of the auditory nerve.

In contrast to conventional hearing aids, which rely primarily on the principles of air conduction, certain types of hearing prostheses commonly referred to as bone conduction devices, convert a received sound into vibrations. The vibrations are transferred through the skull to the cochlea causing motion of the perilymph and stimulation of the auditory nerve, which results in the perception of the received sound. Bone conduction devices are suitable to treat a variety of types of hearing loss and can be suitable for individuals who cannot derive sufficient benefit from conventional hearing aids.

SUMMARY

Many auditory prosthesis recipients are, for all practical purposes, completely deaf without their external sound processors attached and operational. At these times, the recipient's safety, convenience, or quality of life is decreased. Since some recipients choose not to wear their external sound processors at night, they are unable to hear alarm clocks, fire alarms, or even their own baby crying for assistance. There can also be instances where the recipient does not hear sounds even with the processor on. Such sounds can include the high-pitched hiss of leaking cooking gas.

An alert system is able to detect when an auditory prosthesis recipient is wearing her sound processor. When the processor is not worn, the alert system signals a secondary device, such as an accessory, to provide some other form of stimulation to allow the recipient to be made aware of auditory stimuli she is not receiving via the auditory prosthesis. In one example, the alert system can be an application a smartphone or smartwatch that can identify when the recipient is not receiving stimulus from the auditory prosthesis and provide tactile stimulus instead. The recipient can pre-set certain sounds, e.g., alarm clock, smoke alarm, doorbell, for certain types of alerts. Thus, the alert system can effectively "hear" for the recipient. In examples, the system can provide both an audible alert tone as well as a tactile alert for dangerous situations and sounds.

This summary is provided to introduce a selection of concepts in a simplified form that are further described below in the Detailed Description. This summary is not intended to identify key features or essential features of the claimed subject matter, nor is it intended to be used to limit the scope of the claimed subject matter.

BRIEF DESCRIPTION OF THE DRAWINGS

The same number represents the same element or same type of element in all drawings.

DETAILED DESCRIPTION

The technologies described herein enable an auditory prosthesis recipient to be alerted when certain audible stimuli are present in their environment, even though the recipient may not be wearing their auditory prosthesis. For certain recipients, removal or disconnection of a single component of their auditory prosthesis can render them partially or completely incapable of receiving auditory signals. Such circumstances occur either accidentally or deliberately. For example, a recipient can wear an external portion of her auditory prosthesis to bed, but that component can be accidentally knocked off by the recipient while sleeping. Under other circumstances, the recipient can remove the external component to shower. The technologies described herein enable a recipient to be alerted when certain auditory signals are present in their environment, by utilizing an accessory device that can send a tactile or visual stimulus to the recipient at such times when her sound processor is disconnected or otherwise inoperable. In alternative or additional aspects, the technologies contemplate utilization of an auditory prosthesis external portion having limited functionality to send simplified stimuli to a recipient as needed. Regardless of the aspects utilized, the systems described herein enable a recipient to still maintain an awareness of her environment, even when her complete auditory prosthesis is not being worn or is not functioning. This can increase recipient safety, responsiveness to others, and can have other benefits. For clarity, the technologies described herein will be described in the context of a sleeping recipient, although it is clear that there can be other circumstances where a recipient might deliberately or inadvertently remove a portion of their auditory prosthesis, or when the prosthesis is otherwise inoperable.

The technologies described herein can be used in conjunction with various types of auditory prostheses, including active transcutaneous bone conduction devices, passive transcutaneous bone conduction devices, middle ear devices, and cochlear implants. In general, any type of auditory prosthesis that utilizes an external component and an implanted component can benefit from the technologies described herein. The described technologies are useful for auditory prostheses that include head-mounted devices that include microphones, such as so-called button sound processors. Such head-mounted devices can be utilized in conjunction with cochlear implants, bone conduction devices, and other types of auditory prostheses. Additionally, the technology can be utilized in auditory prostheses having components that are worn behind the ear of a recipient. Such devices are called behind-the-ear (BTE) sound processors, and can be connected to a transmission coil worn on the head. Additionally, the technologies described herein can be utilized in totally-implantable cochlear implants. For clarity, however, the technologies disclosed herein will be generally described in the context of a cochlear implant having a sound processor located in a head-mounted, button sound processor.

Figure 1:
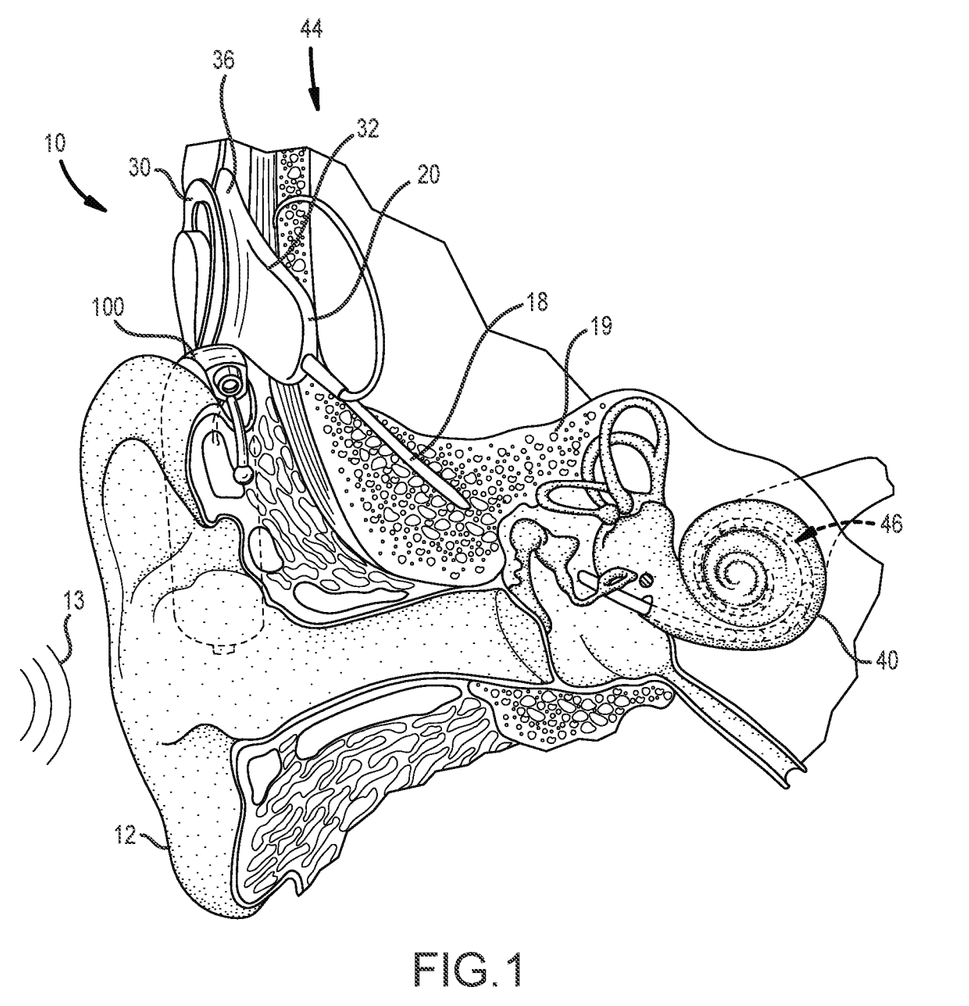
FIG. 1 is a partial view of a behind-the-ear auditory prosthesis worn on a recipient.

Referring to FIG. 1, cochlear implant system 10 includes an implantable component 44 typically having an internal receiver/transceiver unit 32, a stimulator unit 20, and an elongate lead 18. The internal receiver/transceiver unit 32 permits the cochlear implant system 10 to receive and/or transmit signals to an external device. The external device may be a button sound processor worn on the head that includes a receiver/transceiver coil and sound processing components. Alternatively, the external device may be just a receiver/transceiver coil in communication with a BTE device 100 that includes the sound processing components. The implantable component 44 includes an internal coil 36, and preferably, a magnet (not shown) fixed relative to the internal coil 36. Signals sent generally correspond to external sound 13. Internal receiver unit 32 and stimulator unit 20 are hermetically sealed within a biocompatible housing, sometimes collectively referred to as a stimulator/receiver unit. The magnets facilitate the operational alignment of the external and internal coils, enabling internal coil 36 to receive power and stimulation data from external coil 30. The external coil 30 is contained within an external portion 50 such as the type depicted in FIG. 1A. Elongate lead 18 has a proximal end connected to stimulator unit 20, and a distal end implanted in cochlea 40. Elongate lead 18 extends from stimulator unit 20 to cochlea 40 through mastoid bone 19.

In certain examples, external coil 30 transmits electrical signals (e.g., power and stimulation data) to internal coil 36 via a radio frequency (RF) link, as noted above. Internal coil 36 is typically a wire antenna coil comprised of multiple turns of electrically insulated single-strand or multi-strand platinum or gold wire. The electrical insulation of internal coil 36 is provided by a flexible silicone molding. Various types of energy transfer, such as infrared (IR), electromagnetic, capacitive and inductive transfer, can be used to transfer the power and/or data from external device to cochlear implant.

There are a variety of types of intra-cochlear stimulating assemblies including short, straight and peri-modiolar. Stimulating assembly 46 is configured to adopt a curved configuration during and or after implantation into the recipient's cochlea 40. To achieve this, in certain arrangements, stimulating assembly 46 is pre-curved to the same general curvature of a cochlea 40. Such examples of stimulating assembly 46, are typically held straight by, for example, a stiffening stylet (not shown) or sheath which is removed during implantation, or alternatively varying material combinations or the use of shape memory materials, so that the stimulating assembly can adopt its curved configuration when in the cochlea 40. Other methods of implantation, as well as other stimulating assemblies which adopt a curved configuration, can be used.

Figure 1A:
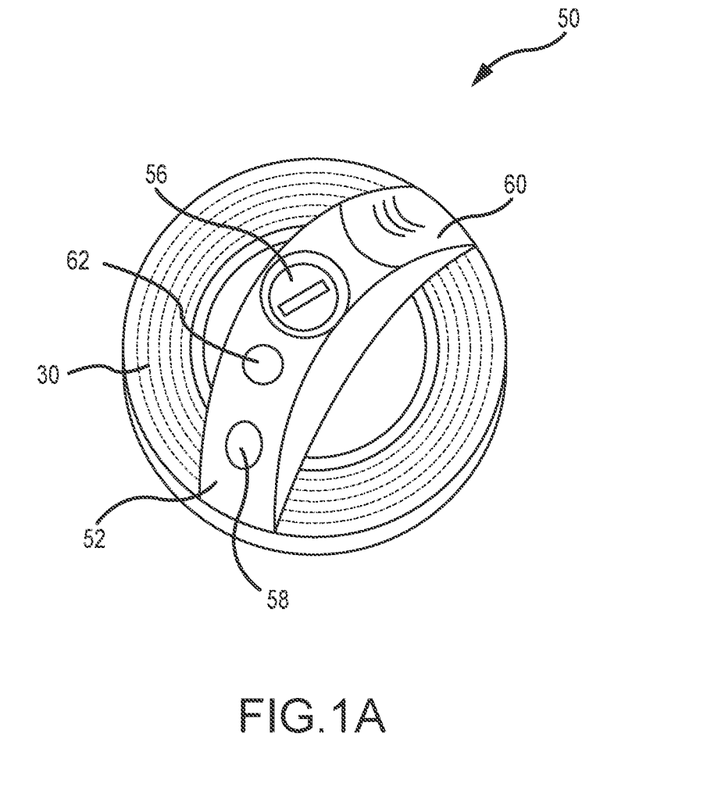
FIG. 1A is a side perspective view of an external portion of an auditory prosthesis.

FIG. 1A is a perspective view of an aspect of an external portion 50 of an auditory prosthesis, in this case, a button sound processor. The external portion 50 includes a body 52 and the external coil 30 connected thereto. The function of the external coil 30 is described above with regard to FIG. 1. The body 52 can include a permanent magnet 56 as described above, which helps secure the external portion 50 to the recipient's skull. The external portion 50 can include an indicator 58 such as a light emitting diode (LED). A battery door 60 covers a receptacle that includes a battery that provides internal power to the various components of the external portion 50 and the implantable portion. An opening 62 allows sound to travel into the body 52 to a microphone or other sound-receiving element disposed therein. The sound is processed by components within the external portion 50. In alternative examples, the microphone, sound processor, and other components can be disposed in the BTE device 100 of FIG. 1, and signals can be sent to the external portion 50 that simply includes the external coil 50 and magnet. The external portion 50, in turn, sends signals to the implantable component 44.

Figure 2A:
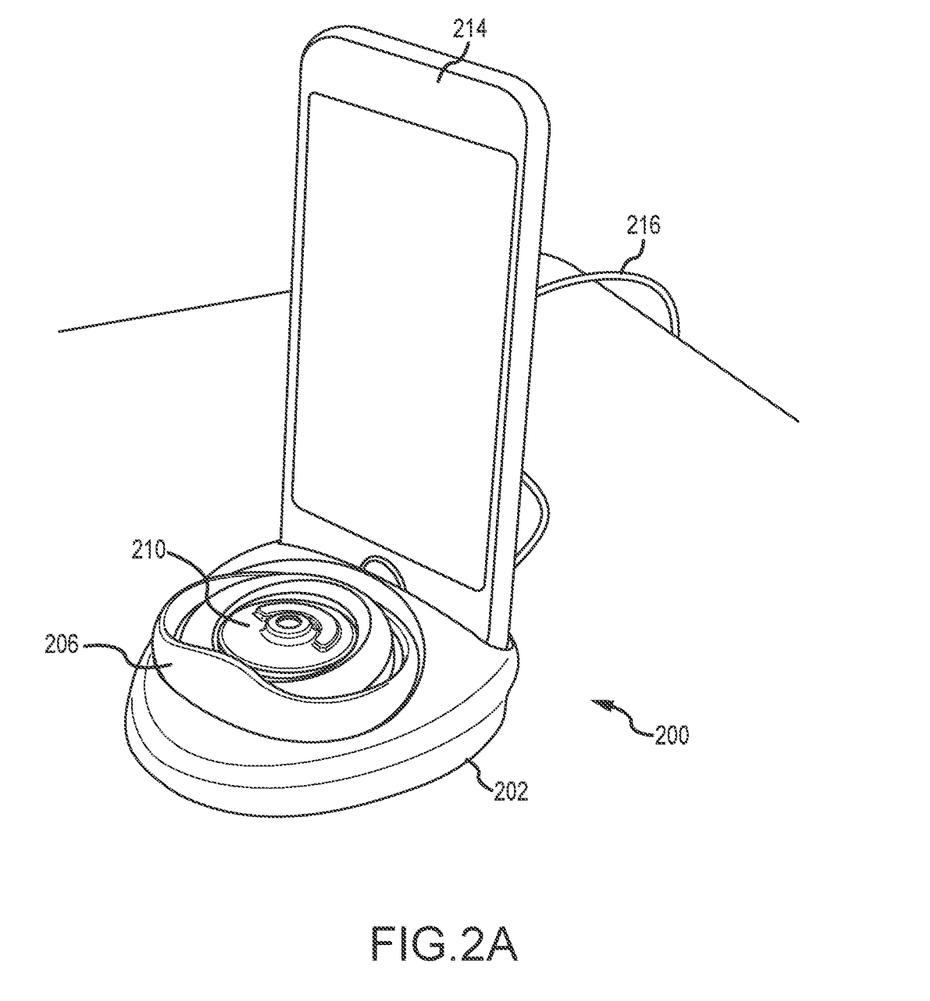
FIGS. 2A and 2B are perspective views of a docking station for use with a system for alerting an auditory prosthesis recipient, in accordance with one aspect of the present technology.
Figure 2B:
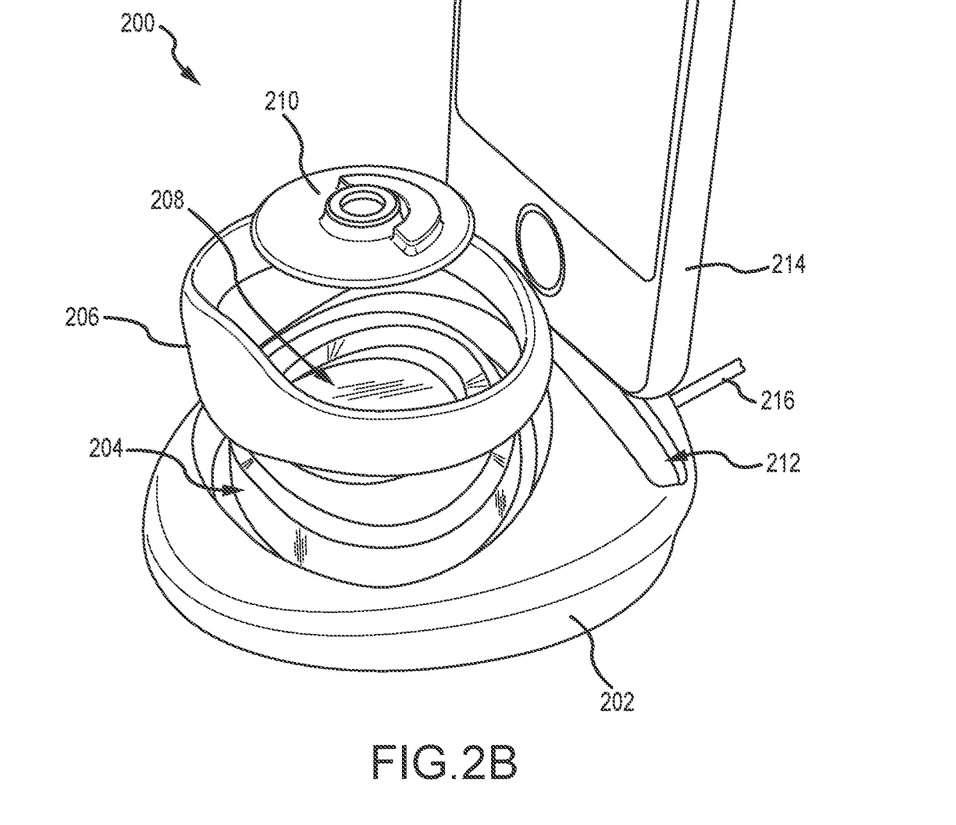

FIGS. 2A and 2B depict perspective views of a docking station 200 for use with a system for alerting an auditory prosthesis recipient, in accordance with one aspect of the present technology. The docking station 200 can be a discrete, stand-alone detection device that provides for storage and charging of components, sound/signal detection, and/or other functionality associated with alert systems such as described herein. In the depicted aspect, the docking station 200 includes a housing 202 that includes various recesses or stations for receiving the various components utilized with the alert system. For example, the housing 202 defines an accessory station 204 for receiving an accessory 206, in this case, a wristband. The accessory 206 can incorporate stimulation elements as described in more detail below. The accessory station 204 can include a wired or wireless charging element for charging a battery on board the accessory 206, and can provide a location to store the accessory 206 when not in use. Although an accessory 206 is depicted as a wristband, other accessories are contemplated. For example, the accessory can be another item worn or contacted by a recipient, for example, a night cap, mouth guard, pillow case, a smartwatch, or article of clothing. In still further examples, the accessory 206 can be an external accessory, such as a smartphone. Certain accessories can utilize a stimulation element and other components integrated therein, or can be manufactured of an e-textile, for example, those manufactured by Intelligent Textiles, Ltd. of the United Kingdom.

The housing 202 defines an auditory prosthesis station 208 for receiving an auditory prosthesis 210. The auditory prosthesis station 208 can include a wired or wireless charging element for charging a battery on board the auditory prosthesis 210, and can provide a location to store the auditory prosthesis 210 when not in use. The auditory prosthesis 210 can be a standard external portion of an auditory prosthesis such as described above in FIG. 1A, which includes all components and functionality to enable complete operation of an implantable portion of an auditory prosthesis. Certain recipients choose to wear their standard external portion while they sleep. In other aspects, however, the auditory prosthesis 210 can be a simplified external portion that has fewer operational components, and that can be manufactured from a softer material that is more comfortable to wear. In that regard, during use while sleeping, a recipient can remove their standard external portion and place it on the auditory prosthesis station 208 overnight for charging. The simplified external portion 210 can be worn throughout the night, then exchanged for the standard external portion in the morning when the recipient wakes. The auditory prosthesis station 208 can incorporate battery charging systems and methods such as those described in U.S. Patent Application Publication No. 2014/0379047, the disclosure of which is hereby incorporated by reference herein in its entirety. Other charging systems and methods are contemplated.

The depicted housing 202 defines a smartphone station 212 for receiving a smartphone 214 or other hand-held device. The smartphone station 212 can include a wired or wireless charging element for charging a battery on board the smartphone 214, and can provide a location to store the smartphone 214, for example on a bedside table. In the depicted aspect, much of the processing power and intelligence for the alert system is resident on the smartphone, e.g., in an application. Power is delivered to the docking station, e.g., to provide charging power to the accessory station 204, auditory prosthesis station 208, and the smartphone station 212, via a cord 216. In other aspects, the docking station 200 can be connected to a personal computer, tablet, or other device via a USB cord, which provides both power to the docking station 200, and the intelligence required to operate the alert system. In other aspects, the docking station 200 can incorporate one or more components such as microphones, transmitters, interfaces, etc., that are utilized in the alert systems described herein.

Figure 3A:
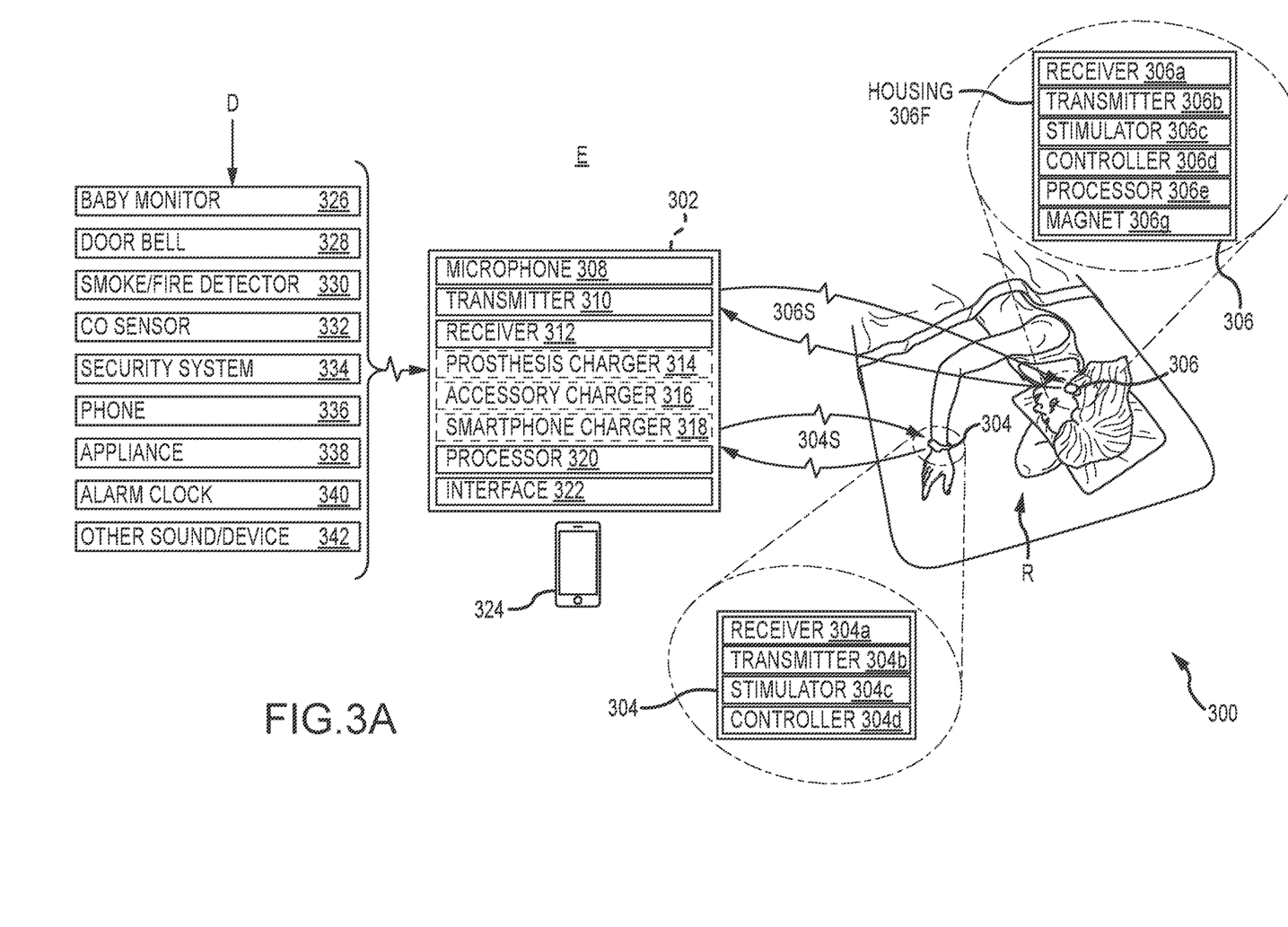
FIG. 3A depicts a system for alerting an auditory prosthesis recipient, in accordance with an aspect of the present technology.

FIG. 3A depicts a system 300 for alerting an auditory prosthesis recipient R, in accordance with an aspect of the present technology. In general, the system 300 includes one or more components that detect, sense, or otherwise receive sounds or signals in an environment E in which the recipient is located. The environment E can be a room, a building, or a general vicinity in which the recipient R is located and where the recipient R can typically be subjected to auditory stimulation from equipment, appliances, other persons, etc. The system 300 includes a sound-detection device 302, an accessory 304 that can be worn or otherwise contact the recipient R, and an auditory prosthesis 306, typically worn by the recipient.

The sound-detection device 302 can include one or more components that enable functionality of the system 300. For example, the sound-detection device 302 can be a docking station, such as depicted elsewhere herein, that includes all the required or desired components necessary for operation of the alert system 300. For a stand-alone detection device 302, a number of components are depicted. A microphone 308 receives sound signals from the environment E. A transmitter 310 can be used to send one or more types of stimulus signals to other components in the system 300, such as the accessory 304 and/or the auditory prosthesis 306. Additionally, if required or desired, the transmitter 310 can be utilized to send communication or other signals to any auxiliary devices D depicted in FIG. 3A. The operation and functionality of these auxiliary devices D are described in more detail herein. Similarly, a receiver 312 is configured to receive signals from the accessory 304, the auditory prosthesis 306, and/or the auxiliary devices D. A prosthesis charger 314, an accessory charger 316, and a smartphone charger 310, can also be disposed on the device 302. A processor 320 can be utilized to process and analyze the various signals and sounds received at the detection device 302 and determine whether alerts should be sent between components of the system 300 based on the signals and sounds. An interface 322, in the form of a graphic user interface, buttons, knobs, etc., can also be incorporated into the device 302.

In certain aspect, the operation of the detection device 302 can be separated between multiple devices. For example, if the device 302 is a docking station such as the type described in FIGS. 2A and 2B, and a smartphone is utilized in conjunction therewith, a number of components can be incorporated into the smartphone. A smartphone 324 is depicted in FIG. 3A. Components incorporated therein can include, for example, the microphone 308, the transmitter 310, the receiver 312, the processor 320, and the recipient interface 322 (e.g., the smartphone touch screen). In another aspect of the system 300 utilizing a smartphone 324, only the processor 320 and recipient interface 322 can be incorporated into the smartphone 324. Thus, the docking station 302 can receive sounds via the microphone 308, and send and receive other signals via the transmitter 310 and the receiver 312. In certain aspects, operation of the system 300, such as processing of the various signals, recipient interfacing, etc., can be performed by the smartphone 324, since the processor 320 and recipient interface 322 are resident thereon. System examples utilizing other distributions of the depicted components between, for example, one or more of a docking station, a smartphone, a personal computer, etc., are contemplated.

Each of the accessory 304 and the auditory prosthesis 306 include a number of components that interact with the detection device 302 and the recipient R. Turning first to the accessory 304, a wristband in the depicted aspect, a number of components are shown. The accessory 304 can include a receiver 304a and a transmitter 304b for receiving and sending signals 304S, respectively, between components in the system (e.g., the transmitter 310 and the receiver 312). The signals 304S can be stimulus signals, status signals, or other operational or diagnostic signals, as required or desired for a particular application. The accessory 304 also includes a stimulator 304c that delivers a tactile stimulus, typically to a skin surface of the recipient R. For example, the stimulator 304c can be a vibration element, which can provide a vibratory stimulus to the recipient R. In another aspect, the stimulator 304c can be one or more contacts for delivering a mild electrical jolt to the recipient R. Alternatively, the stimulator 304c can include a high-intensity LED configured for delivering a strobe or other visual signal. In certain examples, multiple types of stimulators can be incorporated into the accessory 304 as stimulators 304c. A controller 304d in the form of a button, switch, or other element can be incorporated. In other aspects, the controller 304d can include a display, and function as a more advanced interface.

The auditory prosthesis 306 can include a receiver 306a and a transmitter 306b for receiving and sending signals 306S, respectively, between components in the system (e.g., the transmitter 310 and the receiver 312). The signals 306S can be stimulus signals, status signals, or other operational or diagnostic signals, as required or desired for a particular application. The auditory prosthesis 306 also includes a stimulator 306c that delivers a stimulus signal to an implanted portion of the auditory prosthesis in the recipient R. For a cochlear implant, the stimulator 306c can be an external coil that delivers a signal to an implanted coil contained within the implantable portion. A controller 306d in the form of a button, switch, or other element can be incorporated. The auditory prosthesis 306 can be a standard external auditory prosthesis worn during normal operation of an auditory prosthesis. Such a device can include an on-board speech processor, microphone, coil, battery, magnet, and other components for complete operation of an auditory prosthesis. Certain examples, however, contemplate an external portion having simplified construction and functionality. In one aspect, the external portion can include a receiver 306a, transmitter 306b, and stimulator 306c in the form of a coil. The stimulator 306c can be connected to a sound processor 306e that emits only basic signals (e.g., a tone, a ping, a bell, an alarm, etc.) sufficient to awaken the recipient R from sleep or otherwise compel her attention. The housing 306f of the simplified auditory prosthesis 306 can be manufactured of a flexible, compliant material such as silicone that is comfortable to wear while sleeping. Additionally, the simplified auditory prosthesis 306 can include a magnet 306g for holding the simplified auditory prosthesis 306 to the skull.

The system 300 is configured to receive signals from a variety of remote auxiliary devices D that emit sound or electronic signals that can be detected by the detection device 302. Any number of devices D that emit sound or signals are contemplated to be used with the system 300. Such devices include, but are not limited to: baby monitors 326 (microphones used to listen to a baby in a remote location); door bells 328; smoke or fire detectors 330; carbon monoxide sensors 332; commercial or residential security systems 334; telephones 336; appliances 338 (e.g., timers on microwave ovens, door-open alarms on refrigerators); and alarm clocks 340. Additionally, while not emitted necessarily by a device, other sounds 342 such as explosions, gunshots, breaking glass, and so on, can be detected by the device 302 and, if required, used to alert the recipient R.

Detection of signals in the environment E by the device 302 can be via the microphone 308 and/or via the receiver 312. For example, the microphone 308 can detect sounds emitted by any of the devices D, which are then processed by the processor 320 as described in more detail below. Alternatively or additionally, certain of the devices D can emit a signal or trigger that can be detected by the receiver 312 and processed by the processor 320.

Figure 3B:
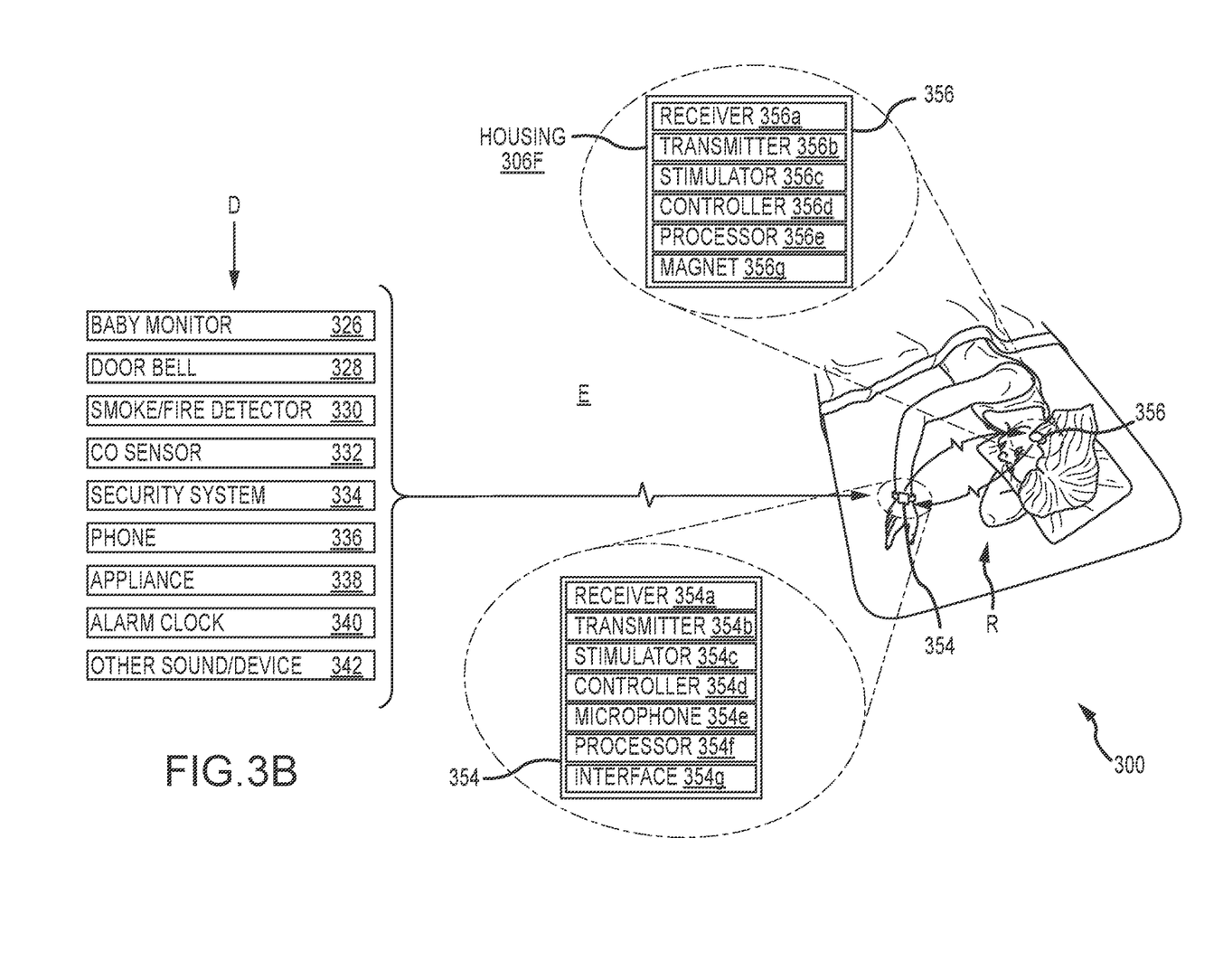
FIG. 3B depicts a system for alerting an auditory prosthesis recipient, in accordance with another aspect of the present technology.

FIG. 3B depicts a system 350 for alerting an auditory prosthesis recipient R, in accordance with another aspect of the present technology. A number of components are depicted and described above with regard to FIG. 3A and are therefore generally not described further. Such components include, for example, the auxiliary devices D and the auditory prosthesis 306. One difference between the system 350 of FIG. 3B and that of FIG. 3A is that the detection device 352 is incorporated into the accessory 354 worn by the recipient R. As described above, the accessory 354 includes a receiver 354a and transmitter 354b, which are used to communicate with both the devices D and the auditory prosthesis 306. The accessory 354 can also include one or more stimulators 354c and a controller 354d as described above. When the accessory 354 also functions as the detection device 352, additional components are utilized. For example, a microphone 354e can be incorporated into the accessory 354 to receive sounds. A processor 354f can process received sounds and signals. An interface 354g can be used by the recipient R to change settings of the accessory 354 and can also be used as the controller 354d. In general, however, the operation of the detection device 352 is similar to that of a detection device that is remote from the recipient R.

Figure 4:
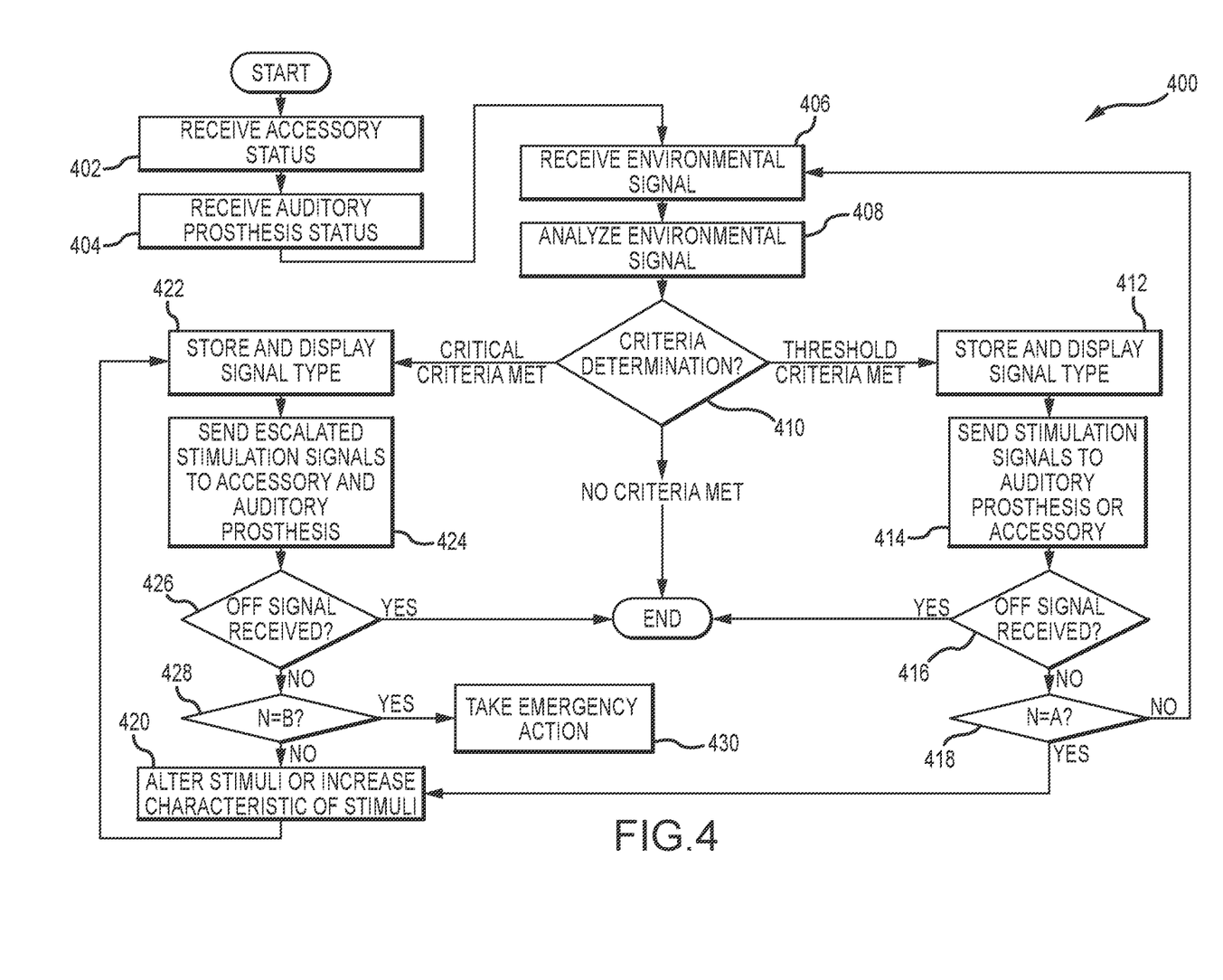
FIG. 4 depicts a method for alerting an auditory prosthesis recipient, in accordance with an aspect of the present technology.

FIG. 4 depicts a method 400 for alerting an auditory prosthesis recipient, in accordance with aspects of the present disclosure. The method 400 begins with the detection of an accessory status, operation 402. An accessory status signal, e.g., can be a signal sent from the accessory to a detection device that indicates that the accessory is in use. Such a signal can be sent by the accessory when the accessory is removed from its station on a docking station. Alternatively, the detection can be an absence of a signal indicating that the accessory is present on its docking station. At operation 404, an auditory prosthesis status is detected. The detection can be receipt of a signal indicating that the auditory prosthesis (e.g., the external portion thereof) is being worn by a recipient (e.g., in contact with its associated implanted coil on an implantable device). In other examples, the detection can correspond to an absence of such a signal. Thus, the detection operation can determine if the auditory prosthesis is not in contact with its associated implanted coil, and/or determine that the auditory prosthesis is in contact, but is in a non-functioning condition (e.g., damaged, no power, etc.). A totally implantable cochlear implant can also be non-functioning is the battery discharges below a certain level during sleep. In that case, the recipient would be unaware that her prosthesis is non-functioning. In that regard, in the context of totally-implantable cochlear implants, a non-functioning implantable sound processor can be detected and stimulation can be send via the accessory (as described below). Technologies that detect separation between a transmission coil and a receiver coil of an auditory prosthesis are well-known in the art and are described, for example, in U.S. Pat. No. 8,452,412, the disclosure of which is hereby incorporated by reference herein in its entirety. Although operations 402 and 404 are depicted only once, other aspects of the method 400 contemplate that the detection can be performed on an intermittent or ongoing basis. Ongoing detection allows the various components of an alert system to regularly determine the status of the other components of the system (for example, detection devices can send a stimulus signal to an accessory if a signal indicates that the auditory prosthesis has fallen off the recipient).

The method 400 continues with operation 406, where an environmental signal is received. The environmental signal can be any signal received by a microphone or a transmitter on the detection device. For example, the environmental signal can be a sound generated by a smoke detector or an electronic signal or trigger emitted by a smoke detector. In another example, the environmental signal can be any signal received by the detection device, including those not generated by devices. Such environmental signals can be explosions, the hissing of leaking cooking gas, dog barking, speech, and so on. Once received, the environmental signal is analyzed in operation 408. Analysis of the environmental signal can include a determination if the signal falls within a type of recognized signal. For example, a sound or electronic trigger signal emitted by a smoke detector can be recognized, while a dog barking cannot be recognized. In such a case, only recognized sounds can be acted upon by the alert system. Analysis can also include a sound volume determination, with sounds having higher volumes being deemed by the alert system to be subject to further analysis. For example, a loud dog bark might be indicative of the recipient's dog barking, while a faint dog bark might be indicative of a neighbor's dog barking outside. Depending on the settings of the detection device, the loud dog bark can be further analyzed and acted upon, while the detection device can ignore the faint dog bark. In still other examples, settings on the detection device can be such that any sound over a certain decibel level can be deemed appropriate for further analysis and alert generation. Such a condition recognizes situations where louder sounds are either (a) generated close by the recipient, or (b) of critical importance, regardless of distance. Sounds generated close to the recipient are likely within the recipient's immediate environment and likely to be of importance to the recipient, while extremely loud sounds can be important simply due to their volume (for example, the sound of a gunshot, regardless of distance from the recipient). It is contemplated that other types of analysis can be performed on received environmental signals and can be categorized, determined, etc., based on recipient settings of the detection device, factory default settings, detection device logical function and memory, sound frequency, sound volume, sound pitch, signal redundancy, signal type, etc. One of skill in the art will appreciate that different methods and/or processes for recognizing and identifying sounds can be incorporated with the aspects disclosed herein to identify and/or classify an environmental signal.

In operation 410, an environmental signal criteria determination is made. In one aspect, a detection device determines whether the detected environmental signal does not meet an alert criteria, meets a threshold criteria, and/or meets a critical criteria. If the environmental signal does not meet any criteria, flow branches NO CRITERIA MET and the program ENDS (returns to START). Such a condition can exist when the detection device receives the sound of a person talking, but determines that the volume of speech is too faint to require an alert (e.g., the person can be talking outside an open window, away from the recipient).

If the environmental signal meets a minimum criteria necessitating an alert, flow branches THRESHOLD CRITERIA MET, into the THRESHOLD CRITERIA loop and the signal type is stored and displayed on an interface on the detection device and/or accessory, operation 412. Storing the signal type allows for a recipient to review past received signal(s) to optimize the functionality of her alert system. Displaying the signal type allows the recipient to quickly determine what type of environmental signal is present, even if groggy due to being roused from sleep. This functionality can be desirable because the recipient can see very quickly that, e.g., a phone is ringing, and can choose to cancel the alert if they do not wish to be disturbed further. In examples, operation 412 can be performed serially or in parallel with operation 414, where one or more stimulation signals are sent to the auditory prosthesis or accessory. The type of stimulus signal sent (and the signal's intended recipient component) is determined based in part on the detections made at operations 402 and 404. For example, if signals have been detected that the auditory prosthesis is not being worn, the detection device can send a stimulus to the accessory instead. In operation 416, an OFF signal can be received, which can stop generation of the alert. Such a signal can be received due to a recipient pressing a controller on her accessory or on the detection device. If a signal is received, flow branches YES to END the alert (and return to START). If no signal is received, flow branches NO to iteration operation 418, where the number or length of alerts associated with this threshold criteria is counted or otherwise measured. If the iteration threshold A is not exceeded (e.g., if the recipient has simply ignored or not been roused by the alert), the alert can terminate and return to operation 406 (or to START) and continue monitoring the environment. If the iteration threshold A has been exceeded, the system branches YES and enters a CRITICAL CRITERIA loop, which is described in more detail below. Entry into the CRITICAL CRITERIA loop can be necessitated if, e.g., the same sound has been repeatedly ignored. Such repeated ignoring on the part of the recipient can be indicative of system malfunction or that the environmental signal is actually critical, even though the recipient set the alert system to ignore such signals. As an example, repeated phone ringing can be indicative of a caller desperately attempting to contact the recipient. Entering the CRITICAL CRITERIA loop at operation 420, the method 400 can alter the stimuli and/or increase a characteristic of the stimuli, based on recipient or device settings. Alteration of the stimuli can include, e.g., emitting an electrical jolt stimulation (instead of a vibration stimulation) from the accessory. Increasing a characteristic of the stimuli can include, e.g., increasing a frequency of vibration of the accessory, or altering the signal sent from the auditory prosthesis so as to increase a perceived pitch of the alert sound. If operation 420 does not generate a response in the recipient, flow continues to operation 422, described below.

Returning to operation 410, if the environmental signal meets a critical criteria necessitating an alert, flow branches CRITICAL CRITERIA MET, into the CRITICAL CRITERIA loop and the signal type is stored and can be displayed on an interface on the detection device and/or accessory, operation 422. Storing the signal type allows for a recipient to review past received sounds to optimize the functionality of their alert system. Displaying the signal type allows the recipient to quickly determine what type of environmental signal is present, even if groggy due to being roused from sleep. The CRITICAL CRITERIA loop can be characterized by one or more operations designed to alert the recipient to important environmental conditions that can be indicative of increased or immediate danger. The operations include but are not limited to, sending of stimuli immediately to both the accessory and auditory prosthesis, immediate alteration of the stimuli or immediate increases in stimuli characteristics, a reduced number of allowed iteration operations, and in certain circumstances, the taking of an emergency action on behalf of the alert system. These operations are described in more detail below.

Operation 422 can occur in serial or in parallel with operation 424, where escalated signals are sent to both the auditory prosthesis and accessory. Such signals are referred to as "escalated" because they are generally of a higher stimulation than those sent in the THRESHOLD CRITERIA loop. The signals can be of the type described generally in operation 420, for example. In operation 426, an OFF signal can be received, which can stop generation of the alert. Such a signal can be received due to a recipient pressing a controller on her accessory or on the detection device itself. If a signal is received, flow branches YES to END the alert and return to START. If no signal is received, flow branches NO to iteration operation 428, where a reduced number or length of alerts associated with the critical criteria is counted or otherwise measured. If the iteration threshold B is not exceeded (e.g., if the recipient has simply ignored or not been roused by the alert), flow branches NO to operation 420 and the CRITICAL CRITERIA loop is repeated. In certain aspects, B can equal ZERO. If the iteration threshold B has been exceeded, flow branches YES and enters operation 430, where the system can take an emergency action. Such emergency actions can include any action designed to more aggressively alert the recipient. Such actions can include, but not be limited to, altering the stimuli so as to cause significant (but not harmful) pain to the recipient, or taking a notification action, in the form of performing an automatic call operation to a remote caregiver or community emergency services, turning on or flashing lights, if the device is integrated into a building management system, etc.

Figure 5:
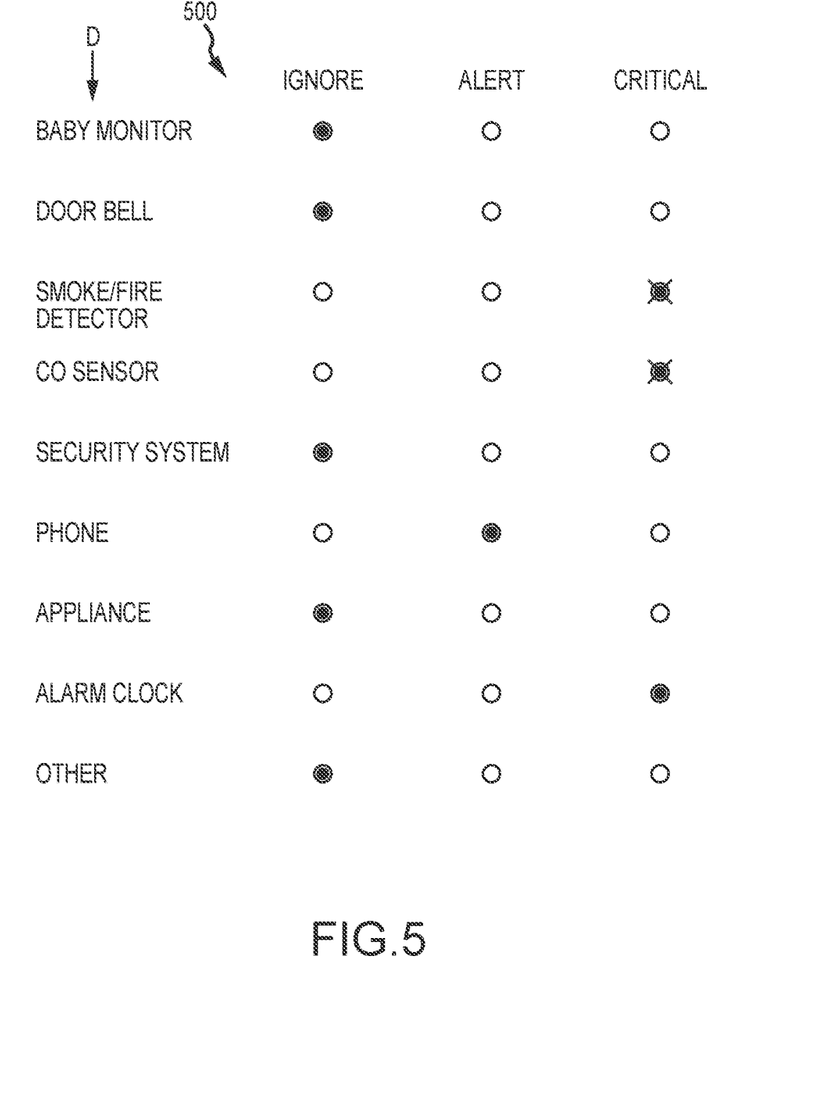
FIG. 5 depicts an interface depicting selected recipient settings for an alert system.

FIG. 5 depicts an interface 500 depicting selected recipient settings for an alert system. A number of devices D, such as the exemplary types identified herein, can be displayed on the interface. For certain devices D, factory settings can default to certain actions. For example, signals received from smoke/fire detectors and carbon monoxide sensors can be set to CRITICAL, and not be changeable by the recipient (and are thus shown "greyed out"). Actions associated with signals received from certain devices D, however, can be set by a recipient, based on recipient preferences and desires. In the depicted aspect, the recipient has set the device to IGNORE a number of devices, as being not present in their environment (e.g., baby monitor) or not important (e.g., doorbell). Here, the recipient has set the device to ALERT for phone calls and CRITICAL for her alarm clock, in order to make her early flight, for example. The recipient can change certain of these settings at any time. The interface 500 can be displayed on a device such as a smartphone, a laptop, a computer, a tablet, etc. that is in communication with the systems disclosed herein.

Figure 6:
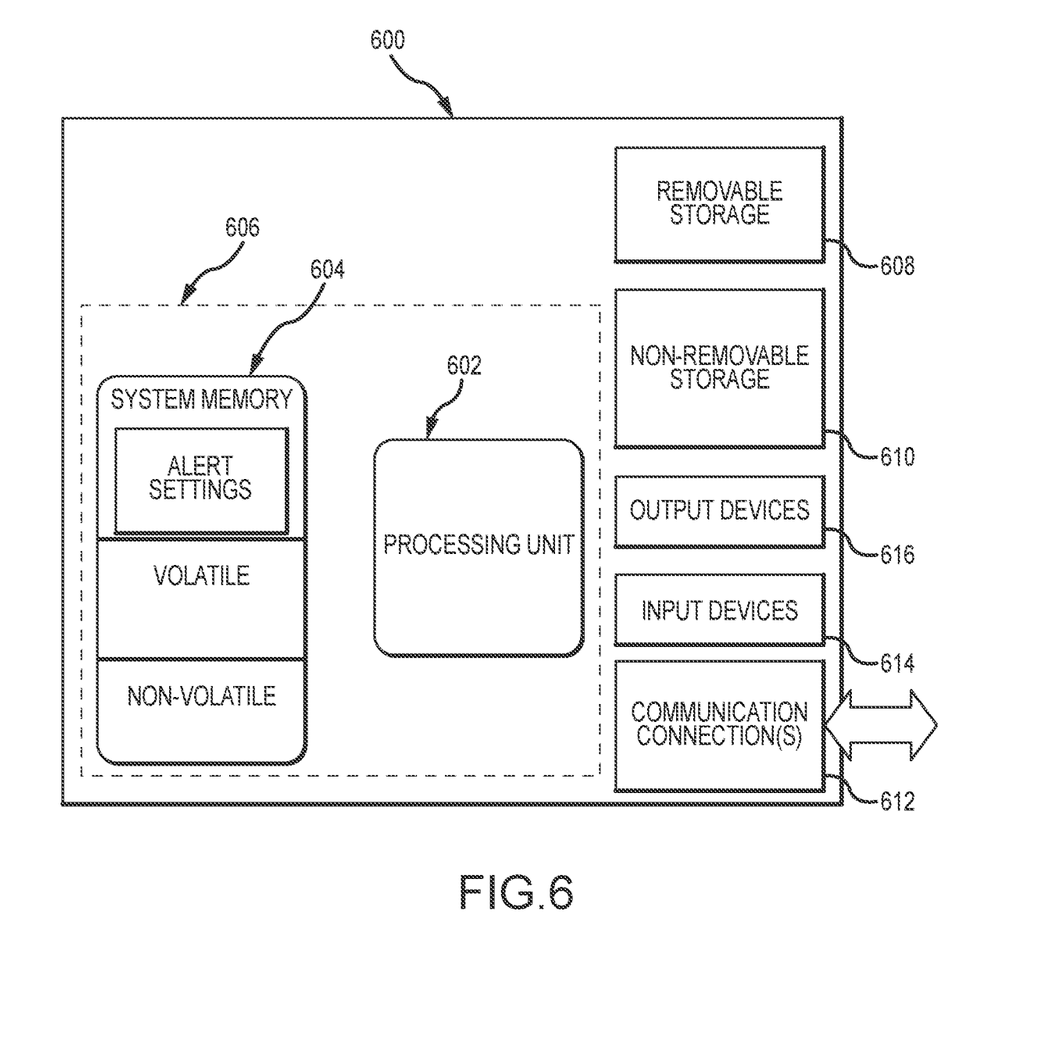
FIG. 6 illustrates one example of a suitable operating environment in which one or more of the present examples can be implemented.

FIG. 6 illustrates one example of a suitable operating environment 600 in which one or more of the present examples can be implemented. This is only one example of a suitable operating environment and is not intended to suggest any limitation as to the scope of use or functionality. Other well-known computing systems, environments, and/or configurations that can be suitable for use include, but are not limited to, auditory prostheses. In examples, an auditory prosthesis includes a processing unit and memory, such as processing unit 606 and memory 604. As such, the basic configuration 606 is part of an auditory prosthesis and/or another device working in conjunction with the auditory prosthesis.

In its most basic configuration, operating environment 600 typically includes at least one processing unit 602 and memory 604. Depending on the exact configuration and type of computing device, memory 604 (storing, among other things, instructions to implement and/or perform the alert functionality disclosed herein) can be volatile (such as RAM), non-volatile (such as ROM, flash memory, etc.), or some combination of the two. This most basic configuration is illustrated in FIG. 6 by dashed line 606. Similarly, environment 600 can also have input device(s) 614 such as a microphone, physical inputs (e.g., buttons), vibration sensors, etc. Other exemplary input device(s) include, but are not limited to, touch screens or elements, dials, switches, voice input, etc. and/or output device(s) 616 such as speakers, stimulation assemblies, etc. Also included in the environment can be one or more communication connections, 612, such as LAN, WAN, point to point, Bluetooth, RF, etc.

Operating environment 600 typically includes at least some form of computer readable media. Computer readable media can be any available media that can be accessed by processing unit 602 or other devices comprising the operating environment. By way of example, and not limitation, computer readable media can comprise computer storage media and communication media. Computer storage media includes volatile and nonvolatile, removable and non-removable media implemented in any method or technology for storage of information such as computer readable instructions, data structures, program modules or other data. Computer storage media includes RAM, ROM, EEPROM, flash memory or other memory technology, solid state storage, or any other tangible or non-transitory medium which can be used to store the desired information. Communication media embodies computer readable instructions, data structures, program modules, or other data in a modulated data signal such as a carrier wave or other transport mechanism and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, RF, infrared and other wireless media. Combinations of the any of the above should also be included within the scope of computer readable media.

The operating environment 600 can be a single device operating in a networked environment using logical connections to one or more remote devices. The remote device can be an auditory prosthesis, a personal computer, a server, a router, a network PC, a peer device or other common network node, and typically includes many or all of the elements described above as well as others not so mentioned. The logical connections can include any method supported by available communications media. Such networking environments are commonplace in offices, enterprise-wide computer networks, intranets and the Internet.

In some examples, the components described herein comprise such modules or instructions executable by operating environment 600 that can be stored on computer storage medium and other non-transitory mediums and transmitted in communication media. Computer storage media includes volatile and non-volatile, removable and non-removable media implemented in any method or technology for storage of information such as computer readable instructions, data structures, program modules, or other data. Combinations of any of the above should also be included within the scope of readable media. In some examples, computer system 600 is part of a network that stores data in remote storage media for use by the computer system 600.

The examples described herein can be employed using software, hardware, or a combination of software and hardware to implement and perform the systems and methods disclosed herein. Although specific devices have been recited throughout the disclosure as performing specific functions, one of skill in the art will appreciate that these devices are provided for illustrative purposes, and other devices can be employed to perform the functionality disclosed herein without departing from the scope of the disclosure.

This disclosure described some aspects of the present technology with reference to the accompanying drawings, in which only some of the possible aspects were shown. Other aspects can, however, be embodied in many different forms and should not be construed as limited to the aspects set forth herein. Rather, these aspects were provided so that this disclosure was thorough and complete and fully conveyed the scope of the possible aspects to those skilled in the art.

Although specific aspects were described herein, the scope of the technology is not limited to those specific aspects. One skilled in the art will recognize other aspects or improvements that are within the scope of the present technology. Therefore, the specific structure, acts, or media are disclosed only as illustrative aspects. The scope of the technology is defined by the following claims and any equivalents therein.

What is claimed is:

1. A method comprising:
   receiving an environmental audio signal while a recipient of an auditory prosthesis is unable to receive auditory signals from the auditory prosthesis;
   determining, with an application of a smartphone, tablet, or personal computer, whether the environmental audio signal meets a threshold criteria; and
   responsive to the environmental audio signal satisfying the threshold criteria, sending a stimulus signal to the recipient of the auditory prosthesis.

2. The method of claim 1, wherein sending a stimulus signal to a recipient of an auditory prosthesis includes:
   sending the stimulus signal to a recipient of an auditory prosthesis via an accessory device worn by the recipient.

3. The method of claim 1, further comprising:
   further responsive to the environmental audio signal satisfying the threshold criteria, storing a type associated with the environmental audio signal; and
   displaying the type to the recipient.

4. The method of claim 1, further comprising:
   detecting a status of the auditory prosthesis,
   wherein the sending of the stimulus is based at least in part on the status of the auditory prosthesis.

5. The method of claim 1, further comprising:
   determining whether the environmental audio signal meets a critical criteria; and
   ending an escalated stimulus signal to the recipient based at least in part on the critical criteria determination.

6. The method of claim 1, wherein determining whether the environmental audio signal meets the threshold criteria includes:
   analyzing sound frequency and sound volume of the environmental audio signal.

7. The method of claim 1, wherein the stimulus signal is a vibratory stimulus signal, electrical stimulus signal, or visual stimulus signal.

8. The method of claim 1, wherein the environmental audio signal is received while the recipient is not wearing the auditory prosthesis, thereby the recipient being unable to receive auditory signals from the auditory prosthesis.

9. A system comprising:
   an accessory comprising a stimulator;
   a detection device comprising a microphone, a transmitter, and a processor, wherein the processor is configured to:
   detect an environmental audio signal with the microphone;
   analyze the environmental audio signal; and
   transmit a signal to the accessory based on the analyzing to cause the stimulator to deliver a perceptible stimulus to a user.

10. The system of claim 9, wherein the accessory comprises a wristband.

11. The system of claim 9, wherein the perceptible stimulus is a vibratory stimulus.

12. The system of claim 9, wherein the perceptible stimulus is an electrical stimulus.

13. The system of claim 9, wherein the perceptible stimulus is a visual stimulus.

14. The system of claim 9, further comprising:
   an auditory prosthesis of the user.

15. An apparatus comprising:
   a non-transitory computer readable medium comprising instructions that, when executed by one or more processors cause the one or more processors to:
   receive an environmental audio signal;
   analyze the environmental audio signal; and
   based on the analyzing, transmit a signal to an accessory to cause the accessory to deliver a perceptible stimulus to a user.

16. The apparatus of claim 15, wherein to analyze the environmental audio signal includes to analyze the environmental audio signal based on recipient settings.

17. The apparatus of claim 15, wherein to analyze the environmental audio signal includes to analyze the environmental audio signal based on sound frequency and sound volume.

18. The apparatus of claim 15, wherein to analyze the environmental audio signal includes comparing the environmental audio signal with a threshold; and wherein to transmit the signal is responsive to the environmental audio signal passing the threshold.

19. The apparatus of claim 15, wherein to analyze the environmental audio signal includes to determine whether the environmental audio signal meets a critical criteria; and
   wherein the perceptible stimulus is an escalated stimulus signal responsive to the environmental audio signal meeting the critical criteria.

20. The apparatus of claim 15, further comprising:
   a smartphone comprising the non-transitory computer readable medium.

* * * * *